US010232159B2

(12) United States Patent
Birchall et al.

(10) Patent No.: US 10,232,159 B2
(45) Date of Patent: Mar. 19, 2019

(54) MICRONEEDLE BASED CELL DELIVERY

(71) Applicants: James Birchall, Cardiff South Glamorgan (GB); Sion Coulman, Cardiff South Glamorgan (GB); Dev Shah, Cardiff South Glamorgan (GB); Benedetta Gualeni, Lovere (IT)

(72) Inventors: James Birchall, Cardiff South Glamorgan (GB); Sion Coulman, Cardiff South Glamorgan (GB); Dev Shah, Cardiff South Glamorgan (GB); Benedetta Gualeni, Lovere (IT)

(73) Assignee: UNIVERSITY COLLEGE CARDIFF CONSULTANTS LIMITED, Cardiff, Wales (GB)

( * ) Notice: Subject to any disclaimer, the term of this patent is extended or adjusted under 35 U.S.C. 154(b) by 0 days.

(21) Appl. No.: 15/122,664

(22) PCT Filed: Mar. 2, 2015

(86) PCT No.: PCT/GB2015/050594
§ 371 (c)(1),
(2) Date: Aug. 31, 2016

(87) PCT Pub. No.: WO2015/132568
PCT Pub. Date: Sep. 11, 2015

(65) Prior Publication Data
US 2017/0065803 A1 Mar. 9, 2017

(30) Foreign Application Priority Data
Mar. 4, 2014 (GB) .................... 1403773.3

(51) Int. Cl.
A61M 37/00 (2006.01)
A61B 10/00 (2006.01)
A61B 10/02 (2006.01)

(52) U.S. Cl.
CPC ..... *A61M 37/0015* (2013.01); *A61B 10/0035* (2013.01); *A61B 10/0233* (2013.01); *A61M 2037/003* (2013.01); *A61M 2037/0023* (2013.01); *A61M 2037/0046* (2013.01); *A61M 2037/0061* (2013.01)

(58) Field of Classification Search
CPC ...... A61M 37/0015; A61M 2037/0023; A61M 2037/003; A61M 2037/0046; A61M 2037/0061; A61B 10/0035; A61B 10/0233
USPC .......................................... 604/506
See application file for complete search history.

(56) References Cited

U.S. PATENT DOCUMENTS 6,743,211 B1 * 6/2004 Prausnitz ........... A61B 5/14514
424/449
2002/0138049 A1 * 9/2002 Allen ................. A61B 5/14514
604/272

(Continued)

OTHER PUBLICATIONS

WO 2010/059605A2, Burton et al., publication date: May 27, 2010.*
WO 2010059605, Burton et al., publication date: May 27, 2010.*

Primary Examiner — Manuel A Mendez
(74) Attorney, Agent, or Firm — Adam Warwick Bell; Matthew Rupert Kaser

(57) ABSTRACT

The invention relates to a device for use in skin improvement or repair, including promoting hair growth, comprising the use of microneedles for the transplantation of cells and a method employing the use of same.

21 Claims, 12 Drawing Sheets

(56) References Cited

U.S. PATENT DOCUMENTS

Figure 1:
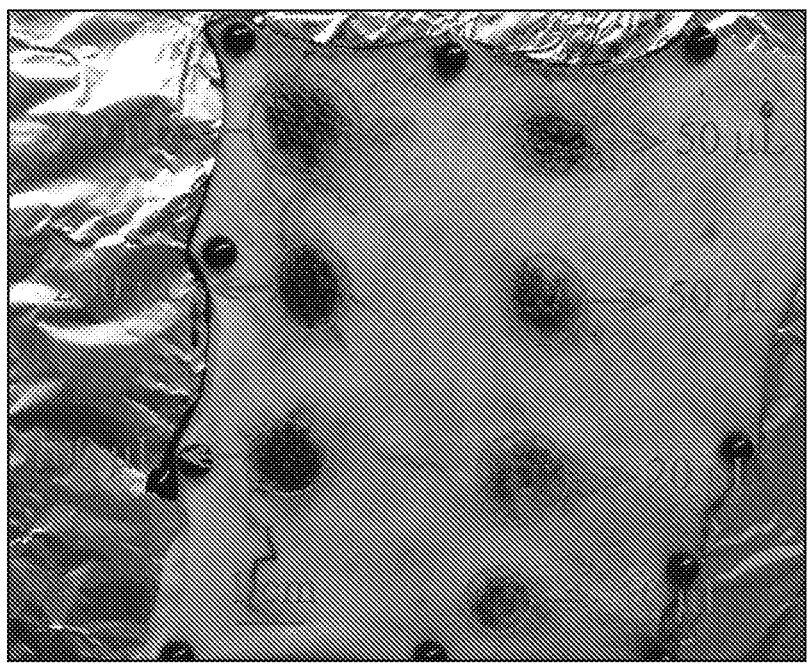

| | | | |
|---|---|---|---|
| 2003/0135167 A1* | 7/2003 | Gonnelli | A61M 37/0015 604/272 |
| 2004/0094503 A1* | 5/2004 | Ozeryansky | A61M 37/0015 216/2 |
| 2012/0201786 A1* | 8/2012 | Tankovich | A61K 35/28 424/93.7 |
| 2013/0071360 A1* | 3/2013 | Silva | C12N 5/0653 424/93.7 |

* cited by examiner

_MICRONEEDLE BASED CELL DELIVERY_

FIELD OF THE INVENTION

The invention relates to a device for use in skin improvement or repair, including promoting hair growth, comprising the use of microneedles for the transplantation of cells and a method employing the use of same.

BACKGROUND OF THE INVENTION

Scientific research has led to extensive developments in cell-based and tissue-based therapies. In recent years, with the advancement of regenerative medicine and tissue engineering, fundamental studies and treatments using living cells have been performed widely.

The field of regenerative medicine is focussed on regenerating damaged tissues and organs in the body by replacing damaged tissue and/or by stimulating the body's own repair mechanisms to heal previously irreparable tissues or organs. This often involves the use of cells or tissue, in cell or tissue therapy, either from the same person (autologous) or from another donor (allogeneic). There are many potential forms of cell therapy, including: the transplantation of stem cells or progenitor cells; the transplantation of mature, functional cells; and the application of modified human cells that are used to produce a needed substance (cell-based gene therapy).

Cell based therapy is targeted at many indications, both medical and non-medical, and in multiple organs and tissues using several modes of cell delivery. Accordingly, the specific mechanisms of action involved are wide ranging. However, there are two main principles by which cells facilitate their desired action:

i) Stem cell or progenitor cell engraftment, differentiation, and long term replacement of damaged tissue. In this paradigm multipotent or unipotent cells differentiate into a specific cell type in the laboratory or after reaching the target site, where they integrate to replace lost tissue, and thus facilitate regeneration and renewal.
  ii) Cells that have the capacity to release cellular factors such as cytokines, chemokines, growth factors or proteins. The delivered cells (via local or systemic administration) remain viable for a relatively short period (days-weeks) and then die. This includes cells that naturally secrete the relevant factors, or which undergo epigenetic changes or genetic engineering that causes the cells to release large quantities of a specific molecule. Examples of this include cells that secrete factors which facilitate angiogenesis, anti-inflammation, and anti-apoptosis.

Whilst it is widely recognized that such cell-based transplantations have application in the medical field to alleviate disease conditions and disorders, current research has led to the increased application of such techniques for non-medical purpose, including use in the cosmetic industry. Many recent cosmetic products and techniques are based on advanced scientific research that includes the use of biotechnology-derived ingredients, nutritional regimens, stem-cell-based products and therapies to regenerate ageing tissues, or use cell and tissue engineering for cosmetic purposes.

Through improved understanding of the structure of the skin and its underlying repair and maintenance processes, researchers are increasingly able to intervene to reduce the effects of premature ageing, improve healing processes or 'enhance' the appearance of skin. The cosmetics and pharmaceutical industries have also expended considerable effort to understand the ageing processes of the skin and to devise countermeasures.

In relation to point ii) above, a recent development is the use and transplantation of one particular skin cell type, the melanin producing cells called melanocytes, which are found in the bottom layer (the stratum basale) of the skin's epidermis. Melanin is the pigment primarily responsible for skin colour, produced through a process called melanogenesis. Numerous cosmetic conditions, or cosmetic effects as a consequence of an underlying disorder, can result in generalized or localized hyperpigmentation (increased skin colour) and hypopigmentation (reduced skin colour) of the skin. Commonly, in the case of localized hypopigmentation, this is attributed to partial or complete loss of melanin such as experienced in:

Pityriasis alba: a sequelae of eczema in which asymptomatic oval pink scaly patches resolve to leave pale macules for some months or longer. Reduced numbers of active melanocytes and a decrease in number and size of melanosomes are seen in affected skin for unknown reasons;

Treatment-induced hypopigmentation: Medications and treatments used to treat various skin conditions can result in lightening of the skin. These include dermabrasion, use of chemical peels, and local steroid injections;

Postinflammatory hypopigmentation (leukoderma): as a consequence of many inflammatory skin conditions, such as skin infection, blisters, burns, cryotherapy, dermal injury with scarring or eczema, loss of pigmentation may occur in the affected area;

Vitiligo: a condition characterised by chronic and progressive depigmentation of areas of the skin. Vitiligo occurs when melanocytes in the basal layer of the epidermis are defective or die. The cause of vitiligo is unknown, but research suggests that different factors might act independently or synergistically to determine the phenotype, including autoimmunity, genetic susceptibility, viral infection, environmental factors, or oxidative stress;

Piebaldism: a rare autosomal dominant disorder of melanocyte development and migration. Common characteristics include a congenital white forelock, scattered normal pigmented and hypopigmented macules and a triangular shaped depigmented patch on the forehead;

Alezzandrini syndrome: a very rare syndrome characterized by a unilateral degenerative retinitis, followed after several months by ipsilateral vitiligo on the face and ipsilateral poliosis; and Melanoma-associated leukoderma: a cutaneous condition characterized by vitiligo-like depigmentation that can occur in patients with cutaneous or ocular melanoma.

Whilst the loss of pigmentation observed in the likes of the above may be of a purely cosmetic concern and only secondary to the underlying pathology leading to same, often the cosmetic dysfunction has a significant negative impact on quality of life. The altered pigmentation is often immediately visible to others and individuals may suffer social and emotional consequences including low self-esteem, social anxiety, relationship problems and depression. Therefore, in addition to finding treatments for the underlying causes of the disease e.g. in the case of vitiligo, it is also paramount to the patient to consider the cosmetic aspects.

In addition to melanocytes, other skin cell types exist with similar potential utility.

Keratinocytes constitute around 90% of the cells of the epidermis, where at the skin surface they produce increasing amounts of keratin and synthesize and extrude lipids into the intracellular space. At the top of the epidermis the cells have differentiated to a cell type that are called corneocytes, which form the outermost skin layer and are constantly shed and replaced by new cells. This differentiation process is tightly controlled to maintain the integrity of the physical skin barrier.

It is known that epidermal melanocytes form a functional and structural unit with neighboring keratinocytes to stimulate melanocyte proliferation, with growth factors produced by adjacent keratinocytes regulating the proliferation and differentiation of melanocytes. Structural changes in keratinocytes may result in loss of melanocytes and evidence suggests that keratinocytes in depigmented epidermis are more vulnerable to apoptosis. Keratinocyte apoptosis will result in reduced expression of keratinocyte-derived factors in depigmented epidermis, resulting in melanocyte death. The relationship between keratinocytes and melanocytes will therefore clearly play a role in skin depigmentation, and the delivery of healthy keratinocytes to depigmented skin, possibly, although not necessarily, in combination with healthy melanocytes (or vice versa), represents a viable strategy for re-pigmentation.

Epidermal stem cells, such as those in the stratum basale or hair follicle, have attracted similar interest from the cosmetics industry and various companies are already exploring their potential for skin-care products, for example, skin regeneration and repair, or anti-ageing products that contain proteins derived from specialized stem-cell lines that affect specific receptors in both fibroblasts and keratinocytes that increase the production of collagen.

Dermal fibroblasts produce collagen (type I, type III and type VII), elastin, hyaluronic acid and matrix metalloproteinases and therefore are essential in forming elongated fibres and extracellular matrix. Dermal fibroblasts produce the structural components that unite separate cell layers and allow epithelial cells of the epidermis to join together to form upper skin barrier layers. The cells also allow skin to recover from injury. For this reason, transfer of dermal fibroblasts has been used cosmetically as anti-ageing and scar remodeling products. Autologous (self) fibroblasts are also being used to treat skin wrinkles, scars, folds and depressions and for lip augmentation. The advantage of using fibroblasts over direct collagen injection relates to the breaking down of collagen protein by endogenous enzymes.

Therefore, the potential for transplantation of cells is readily recognized in the field. A plethora of techniques have thus been developed for delivering cells. For example, to target depigmentation, the transfer and/or culture of target cells, such as keratinocytes, fibroblasts, or melanocytes, from pigmented (normal unaffected skin) to depigmented skin has been tested.

US20100310526 discloses a method for increasing or intensifying the pigmentation of skin, by the application of melanocyte precursor cells from hair root sheaths onto the depigmented area. It is disclosed that keratinocyte precursor cells are also applied to the depigmented area. The procedure requires the recipient site is dermabraded (surgical skin planing) before the application of a cell solution.

US20120064049 discloses a method for the regeneration of aged skin for cosmetic purposes and for the prevention of skin diseases, using stem cells from hair root sheaths and/or keratinocyte and melanocyte precursor cells. According to this method, before the application of the cell solution the epidermis at the recipient site needs to be physically or mechanically ablated, preferably by means of superficial dermabrasion, laser treatment (fraxel laser), or superficial needle puncture (dermaroller).

US20110150848 discloses a method for producing a transplantable cellular suspension of living tissue for grafting to a patient using the ReCell® Spray-On Skin™ system. The method requires harvesting donor tissue from the patient (4 cm$^2$ biopsy, thickness 150-200 µm), performing in-theatre preparation of a spray-on suspension consisting of cells derived from the biopsy, and applying this suspension immediately over the recipient graft site, on a surface up to 80 times the size of the biopsy. The recipient site needs to be dermabraded or laser-treated before treatment. The ReCell suspension contains basal keratinocytes, melanocytes, fibroblasts and Langerhans cells. The metabolically responsive epithelial cells migrate across the wound surface, leading to regeneration of skin of normal colour and texture.

However it is apparent that the many existing methods for transferring tissue (skin grafting) or cells have associated inherent problems, including:

Koebner phenomenon: This is the development of disease at sites of trauma. For example if someone with psoriasis scratches themselves, they can develop the phenomenon along the skin that was scratched.

Scarring: The transfer of skin via grafts or punches leads to defects, trauma and scarring to skin at a second site.

Skin preparation: Cells can only be transplanted onto prepared skin, i.e. skin that has had its epidermis removed via invasive techniques such as dermabrasion.

Pain: These invasive techniques can be very painful and are not without risk.

Infection: Techniques such as dermabrasion cause major barrier defect and increase the risk of infection.

Skill: Methods are heavily dependent on the skill of a surgeon to carry out the procedure.

Recovery: current procedures require 1-2 weeks recovery.

There is a real unmet need to find more efficient, pain free and cost-effective technologies to repair the skin and permit transfer of cells into same thus achieving a better cosmetic outcome (e.g. 80% or more re-pigmentation without scarring).

Heretofore it has not been shown that cells can be successfully delivered using microneedles. Unexpectedly, the inventors have determined that cells can be injected into surface layers of the skin using fine bore microneedles with no observed loss of viability. Moreover, using a similar such approach, it has been found that cells can be extracted from the skin and that these extracted cells are viable in culture.

The present invention therefore concerns a new minimally-invasive method for the repair of the skin comprising step a) the extraction and step b) the transfer and delivery of skin cells, such as melanocytes, fibroblasts or keratinocytes, using microneedles (MNs), including the targeting of a cellular suspension of freshly extracted, or cultured, cells to the skin. Notably, different layers of the skin can be targeted as the cells will reposition to the appropriate area.

Microneedles are micron-sized, needle-like projections often, but not always, organized in an array of a defined geometric pattern on a planar base plate. They are an established technology currently being exploited for the targeted intra-epidermal and intradermal delivery of drugs and vaccines. Due to their microscopic dimensions MNs do not penetrate skin deep enough to cause any significant pain, bleeding or scarring, as demonstrated through numerous clinical trials. Application of MNs to the skin surface results in penetration of the outer skin barrier, the stratum corneum (SC), and the creation of multiple transient micro-pathways that permit the delivery of materials without impinging significantly on nerves or blood vessels.

Most notably, the micron-scale dimensions of the microneedle shafts allow for simple and direct application into skin that does not require professional training.

A pilot study by a team at Cardiff University has shown the minimally invasive nature of microneedles, compared with conventional hypodermic injection, demonstrating that microneedles caused significantly less pain than normal needles. Further, advantageously, following withdrawal of the microneedle the induced disruptions in the skin surface rapidly reseal thus leaving minimal or no scarring and minimal barrier defect.

This disclosed method therefore paves the way for a new minimally-invasive and pain-free approach wherein cells can be extracted and delivered to the various layers of the skin using microneedles, with little or no recovery time required. There would be no need for highly trained surgeons and expensive equipment to perform the procedure, making the procedure more affordable. Additionally, the use of microneedles minimizes scarring with no perceived change in skin texture or pigment, and given the minimal invasiveness of the technology, the need for prior treatment of the targeted areas is circumvented.

STATEMENTS OF INVENTION

According to a first aspect of the invention there is provided a device for skin improvement or repair comprising: a plurality of microneedles attached to or integral with a supporting base member and arranged in at least one circular pattern on same.

Reference herein to a circular pattern includes reference to a round or elliptical pattern or indeed in some embodiments a 'circle' with relatively angular corners as provided by a pentagon, hexagon, octagon or the like. Thus reference herein to a circular pattern includes reference to a continuous line of adjacent microneedles which may be separate or contiguous.

Reference herein to microneedle is reference to any fine, minimally invasive structure or projection typically less than 1 mm in length and most suitably, but not necessarily, hollow, most typically but not exclusively said microneedle is also straight or curved, further said microneedle is tapered, barbed, bevelled or hooked at its tip.

In a preferred embodiment of the invention said base member is adapted for attachment to, or attached to, a manipulating member, such as a handle or syringe, whereby a user can extract cells from said skin, ideally by scraping in a circular fashion or depressing and rotating said device, against a target area of skin.

Preferably said microneedles are either solid or hollow, although hollow is preferred where said device is to be used for both cell extraction and injection (or replacement). More preferably still said microneedles are straight, curved, hooked or barbed. Indeed, any suitable microneedles having the requisite length and diameter to extract and/or inject the desired cell(s) can be used in accordance with the invention herein disclosed. As will be appreciated by those skilled in the art, the nature of said microneedles is to provide optimum extraction and injection, of certain cells resident in certain layers. Therefore, depending upon the nature of the cell to be extracted and/or tissue layer of the skin to be injected, the physical parameters such as, but not limited to, the length and/or diameter of the microneedles can be varied accordingly to achieve the desired technical effect i.e. to penetrate skin to specific and superficial depths. This will also depend accordingly on the region of the body from which the cells are extracted, as the relative skin layer composition can vary from one region to the next, thus routine changes can be made to the needles to ensure the correct skin layers are extracted from and/or injected into.

However, in a preferred embodiment of the invention, ideally where said microneedles are to be used for injection (or replacement) of melanocytes said microneedles are hollow and have a bore size of between 60-150 µm diameter, including all 1 µm intervals there between, and ideally 75-150 µm diameter needles, including all 1 µm intervals there between, most ideally at least 75 µm diameter.

In a further preferred embodiment of the invention a plurality of concentric circular patterns of microneedles are provided on said base member and, ideally, two or more such circular patterns are provided.

In yet a further preferred embodiment said microneedles are attached to or integral with said base member so that their longitudinal axis is normal to the supporting axis of said base member. Alternatively, said microneedles are attached to or integral with said base member so that their longitudinal axis is at an angle to the supporting axis of said base member and ideally at an angle that results in said microneedles splaying outwards with respect to the supporting axis of said base member.

Preferably, between 6 and 48 microneedles, ideally between 12 and 36 microneedles, are used in each circular pattern and, ideally, 24 microneedles are used in one outer concentric circular pattern and 12 microneedles are used in one inner concentric circular pattern. Other preferred numbers of microneedles may be used and a plurality of circular concentric patterns may be provided on said base member.

Most preferably said microneedles are between 250 µm and 1000 µm in length, including all 1 µm intervals there between, most ideally about 750 µm.

More preferably still said microneedles are made from silicon or steel. Alternatively, said microneedles are made from polymers, co-polymers, polysaccharides or sugar materials such as SU-8, PMMA, polycarbonate, carboxymethylcellulose, polycaprolactone, PLGA, dextran, dextrin, PVA, PVP or maltose.

Reference herein to skin improvement or repair refers to any process whose purpose is to improve functionality of the skin, overcome defects or achieve a desired particular outcome such as appearance or restoration. This may include, but is not limited to, skin re-pigmentation, skin smoothing, skin firming, skin radiance, skin plumping, skin regeneration, improved or enhanced scar and wound repair, improved skin barrier functionality, improved skin elasticity, hair growth, extracellular matrix stimulation including production of collagen, angiogenesis and re-epithelialisation, or the like.

Reference herein to extraction/extracted is reference to the use of said microneedles to remove cells from the preferred layers of the skin as disclosed herein by, for example but not limited to, withdrawal through said microneedles by negative pressure, absorption of said cells by said microneedles, collection into microneedle bores after skin insertion (a microscopic cell biopsy) or alternatively scraping in a linear fashion a layer of the skin with said microneedles or depressing the microneedles into the skin and moving them in a circular fashion.

According to a second aspect of the invention there is provided a method for skin improvement or repair comprising:
  a) extracting with a plurality of microneedles attached to a supporting base member and arranged in at least one circular pattern on same at least one cell from a first area of skin of an individual to be treated; and b) injecting with at least one hollow microneedle, having a bore size between 60-150 µm in diameter, said cell(s) into a second area of skin;

whereby said second area of skin is improved by the transplantation of said cell(s) therein.

In a preferred embodiment of the invention said bore size is between 75 and 150 µm, including all 1 µm intervals there between, most ideally at least 75 µm diameter.

In a further preferred embodiment of the invention said injecting also involves the use of a single microneedle or a plurality of microneedles attached to a supporting base member and where a plurality of microneedles are provided they are arranged in a row, a rectangular array or at least one circular pattern on same, but in this instance said microneedles are hollow and have a bore size of between 60-150 µm, ideally between 75-150 µm diameter, including all 1 µm intervals there between, most ideally at least 75 µm diameter.

In yet a further preferred embodiment still, the same microneedles are used for step a) and step b). Alternatively, different microneedles are used for each step depending upon the cells to be extracted and tissue to be targeted.

In a preferred embodiment of the first aspect of the invention, said method is cosmetic.

In yet a further preferred embodiment of this aspect of the invention, as will be appreciated by those skilled in the art, said cell could be any one or more cell type resident in the skin and in the superficial layers that could reasonably be expected to be extracted by use of microneedles whilst, ideally, not compromising the cosmetic and pain considerations of the invention as herein disclosed. This includes, but is not limited to, a cell from the epidermal and dermal layers, including a hair follicle. Such cell further include a melanocyte, keratinocyte, dermal fibroblast, corneocyte, Langerhans cell, dermal dendritic cell, epidermal stem cell such as epidermal keratinocyte stem cell, Merkel cell, mast cell, macrophage, T-cell, dermal sheath cell or follicular outer root sheath cell, or the like.

Most ideally, said cell is selected from the group comprising: a melanocyte, keratinocyte, dermal fibroblast, epidermal stem cell and follicular outer root sheath cell.

In yet a further preferred embodiment of this aspect of the invention, said method comprises the extraction and/or injection of a single cell type from the skin surface such as but not limited to melanocyte or a number of melanocytes. Alternatively, and more ideally, said method comprises the extraction and/or injection of at least two cell types, such as but not limited to a combination of a melanocyte and keratinocyte and, ideally a combination of a melanocytes and keratinocytes.

In a preferred embodiment of this aspect of the invention, said cell(s) is/are injected into the viable epidermis, papillary dermis and reticular dermis layers. However, as will be appreciated by those skilled in the art, depending upon the nature of the cell to be injected and the result to be achieved, said cell can be injected into any layer of the skin with equal effect. For example, in the case of the injection of one or more melanocytes for skin re-pigmentation said cells would be preferably injected into the supra basal epidermal layer.

In a preferred method of the invention steps a) and b) are performed sequentially and step b) is undertaken after or shortly after step a) has been undertaken.

In a preferred embodiment of this aspect of the invention, said method comprises extracting at least one cell, or more ideally, a plurality of cells.

In the case where a plurality of cells are extracted, advantageously said cells can be separated further into the single cell types using techniques well known to those skilled in the art.

In yet a further preferred embodiment of the second aspect of the invention, steps a) and b) are performed on the same person i.e. said cell(s) injected in step b) is/are autologous (from the same individual as the extracted cell(s) in step a).

Alternatively, steps a) and b) are performed on different people i.e. said cell(s) injected in step b) is/are allogeneic (from a different individual to that/those from whom the cell(s) in step a) was/were extracted). Additionally, said cell(s) extracted in step a) may be xenogeneic (i.e. cells extracted from different species), such as but not limited to mammals, and injected into the skin of a different animal such as a human. As will be appreciated by those skilled in the art, such cell(s) will be need to be immunologically compatible, or modified such that they do not elicit an immunogenic response.

Most preferably, said cell(s) in step b) is/are autologous to the cell(s) with respect to step a).

In yet a further preferred embodiment of the invention, said method further comprises the step of in vitro/ex vivo culturing the cell(s) extracted in step a) prior to their injection in step b) into a patient/person. As will be appreciated by those skilled in the art, certain uses may require a greater number of cells to be injected than can be extracted, or the outcome of the method may be more favourable if a greater number of cells is used. Therefore, cells can be cultured and expanded in vitro using cell culture techniques well known to those skilled in the art. Additionally, said culture can be used to select the cells that are desired to be grown, such as through the use of selective growth media, to promote culture of a selected cell type, which is dependent upon said pre-selected culture conditions.

Additionally, as will be appreciated by those skilled in the field, said cells can be stimulated with appropriate cell culture factors, supplements, proteins, growth factors or the like to result in a preferred cell phenotype and/or differentiation of the cells into a pre-selected phenotype, which phenotype is dependent upon said pre-selected culture conditions.

Further, said cells may be genetically modified such that they show altered protein expression (e.g. increased melanin or collagen expression) or reduced immunogenicity or the like, using techniques known to those skilled in the art such as recombinant nucleic acid (DNA or RNA) techniques to incorporate recombinant material into said cells either indirectly through a vector system or directly through microinjection, macro-injection and micro-encapsulation techniques.

According to yet a further preferred second aspect of the invention, said method in steps a) and b) are repeated for all areas of the skin for which improvement or repair is desired. Moreover, said method can be repeated as necessary for the same area after a defined time period in order to improve or maintain the overall outcome desired.

According to yet a further preferred method of the invention, said extracted and/or cultured cells are preserved for long term use using any suitable means known to those skilled in the art, such as but not limited to, liquid nitrogen storage. Advantageously, in this further preferred method of the invention, said preserved cells can be used for repeated procedures whereby measured amounts of the preserved cells are repeatedly used under step b) above to effect improvement or repair of skin. In this way the need to repeatedly undertake step a) above is circumvented.

According to a further aspect of the invention there is provided a method for promoting hair growth comprising:
a) extracting with at least one microneedle at least one dermal sheath cell from a first area of scalp skin of an individual to be treated; and
b) injecting with at least one microneedle said cell(s) into a second area of scalp skin;
whereby said second area of skin is treated by the transplantation of said cell(s) therein such that hair growth is encouraged.

In this preferred method of the invention step a) involves extracting, with a plurality of microneedles attached to a supporting base member and arranged in at least one circular pattern on same, at least one dermal sheath cell from a first area of scalp skin of an individual to be treated.

Preferably also in this preferred method of the invention step b) involves injecting with at least one hollow microneedle, having a bore size between 60-150 μm diameter, including all 1 μm intervals there between, and ideally between 75-150 μm diameter, most ideally at least 75 μm diameter, said cell(s) into a second area of skin.

In this preferred embodiment of the invention, due to the presence of melanocytes in the developing dermal sheath cells hair re-growth can be of a pigmented nature and so the method not only alleviates baldness but also ameliorates premature greying.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 2:
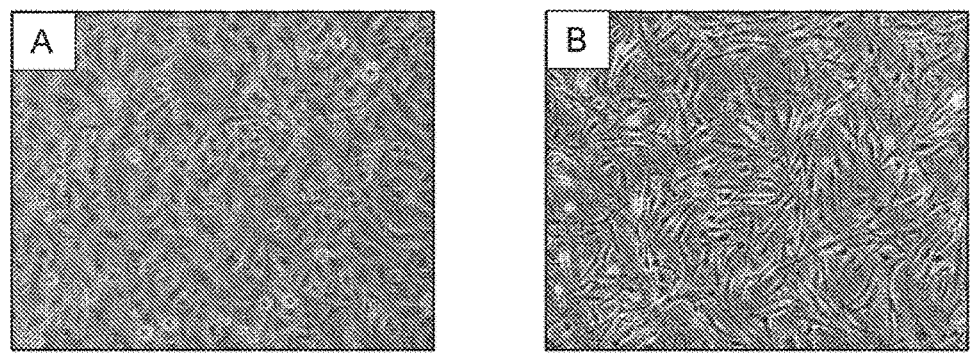
Figure 3:
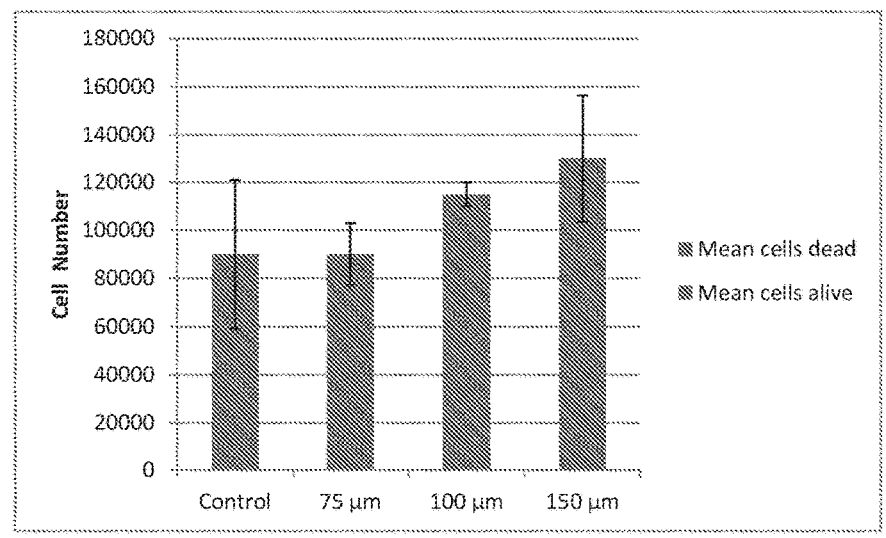
Figure 4:
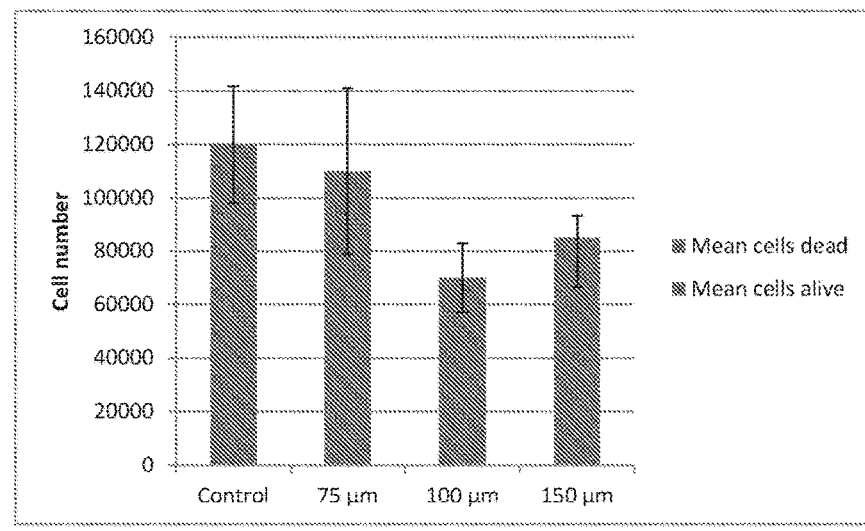
Figure 5:
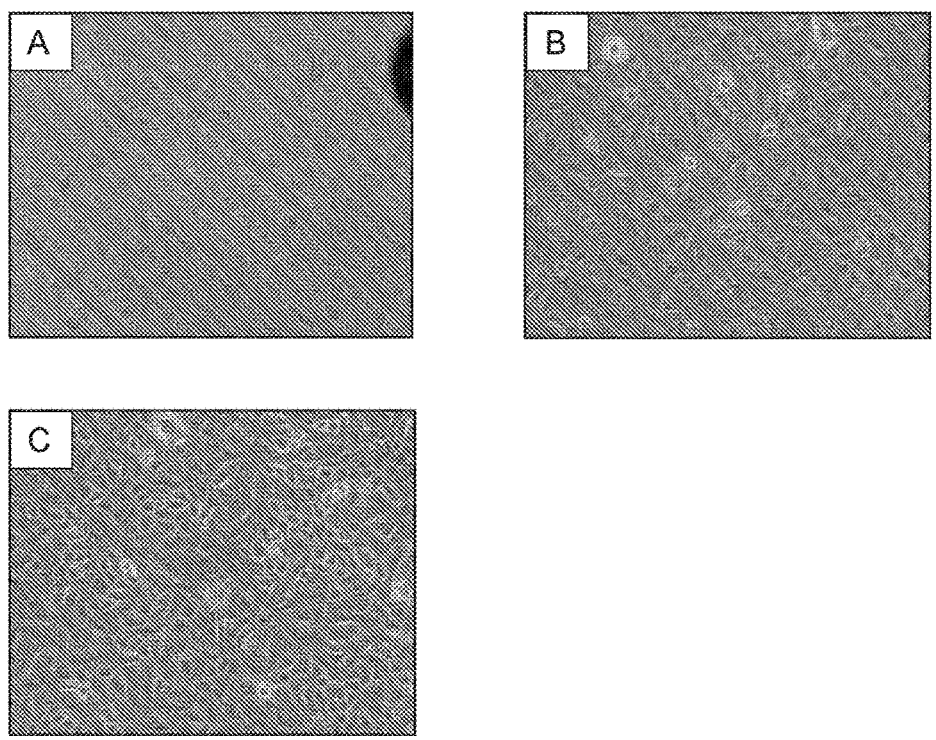
Figure 6:
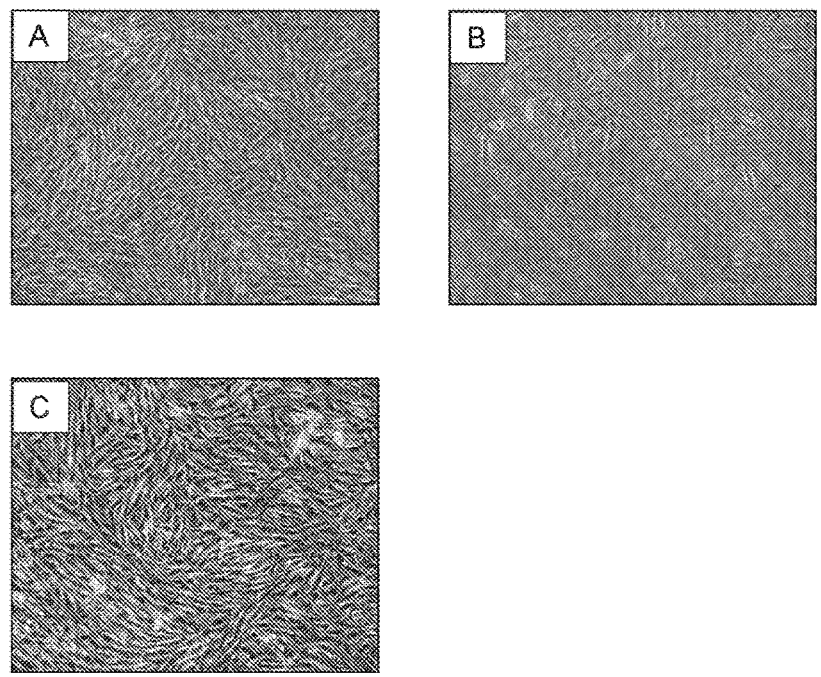
Figure 7:
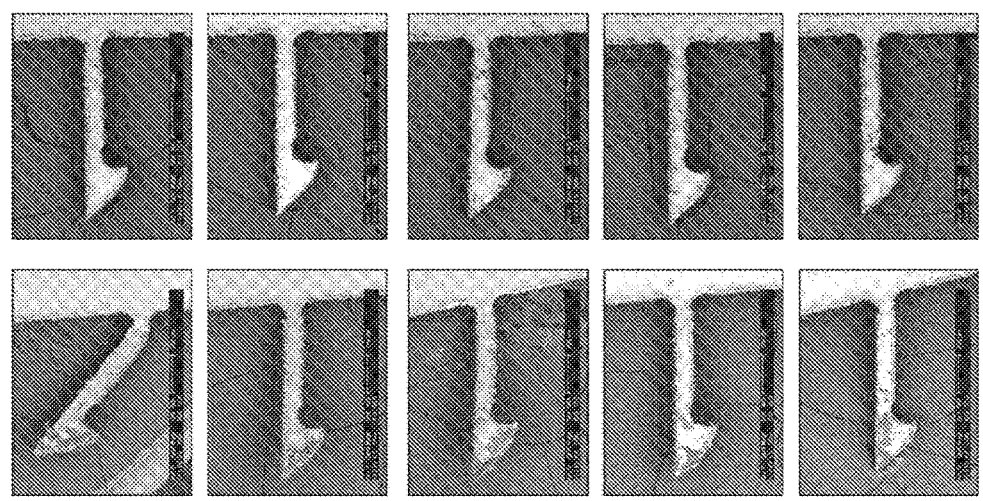
Figure 8:
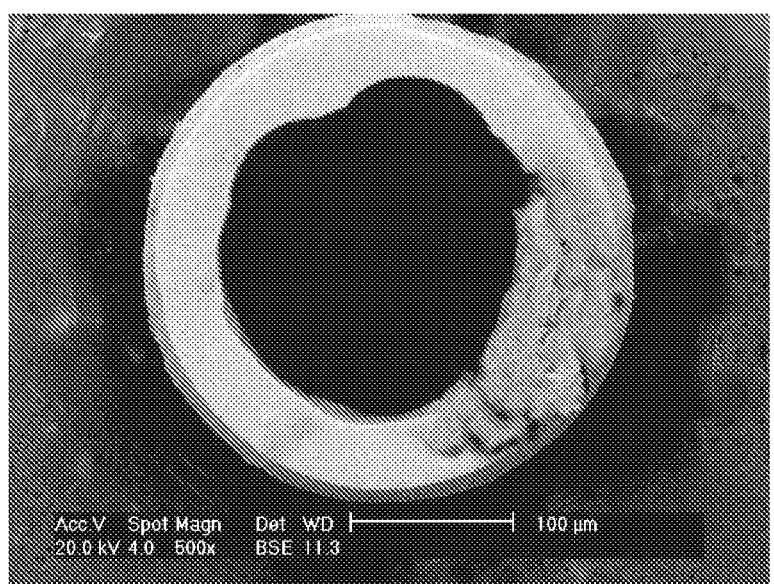
Figure 9:
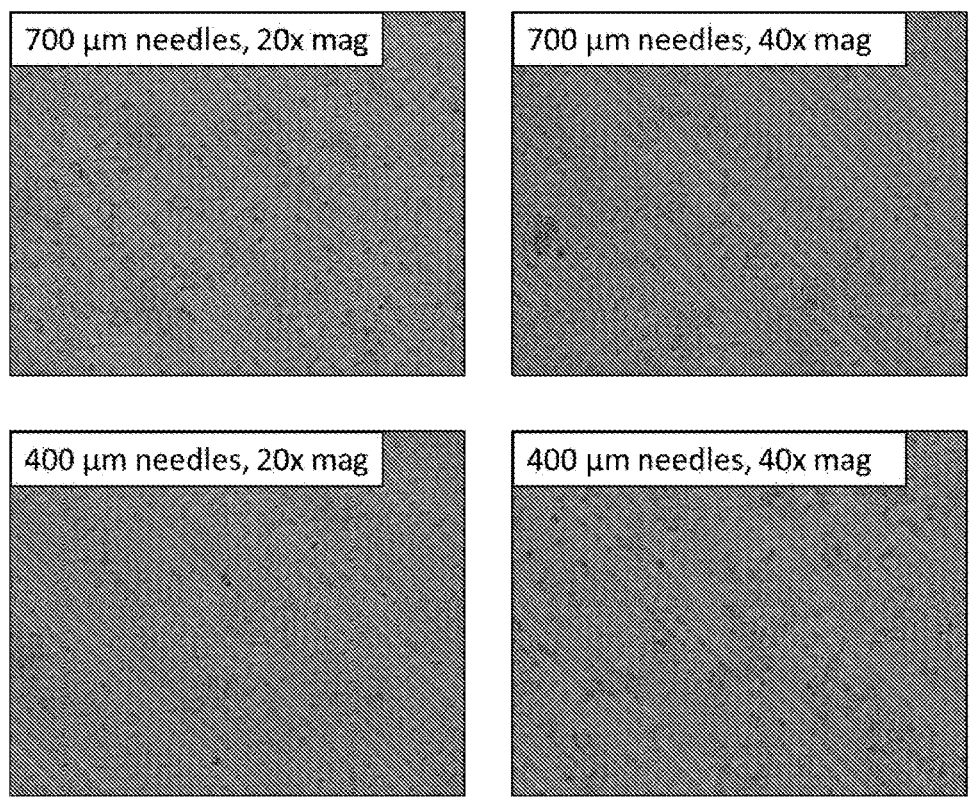
Figure 10:
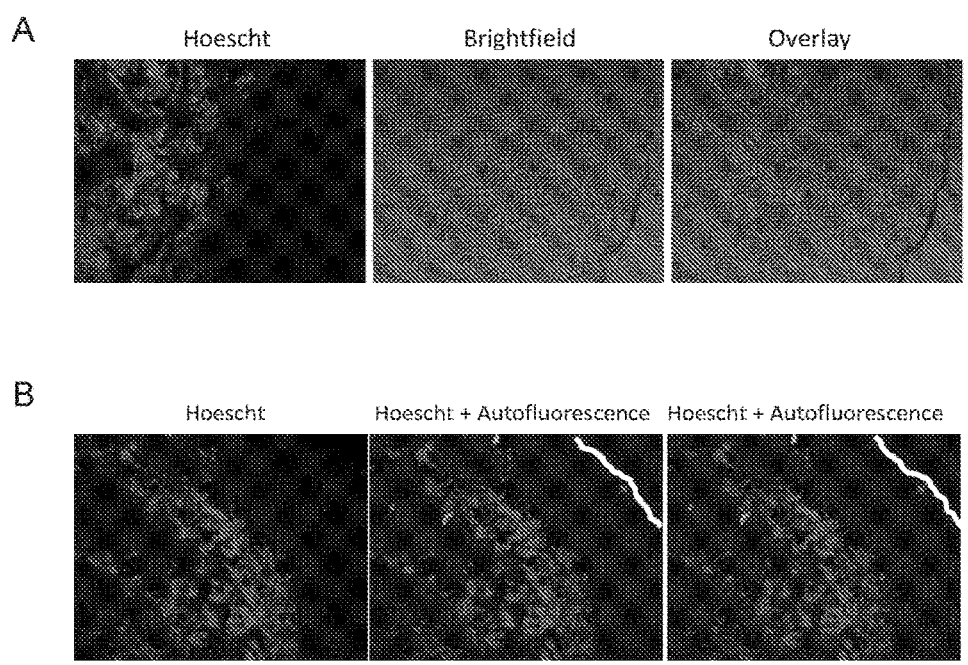
Figure 11:
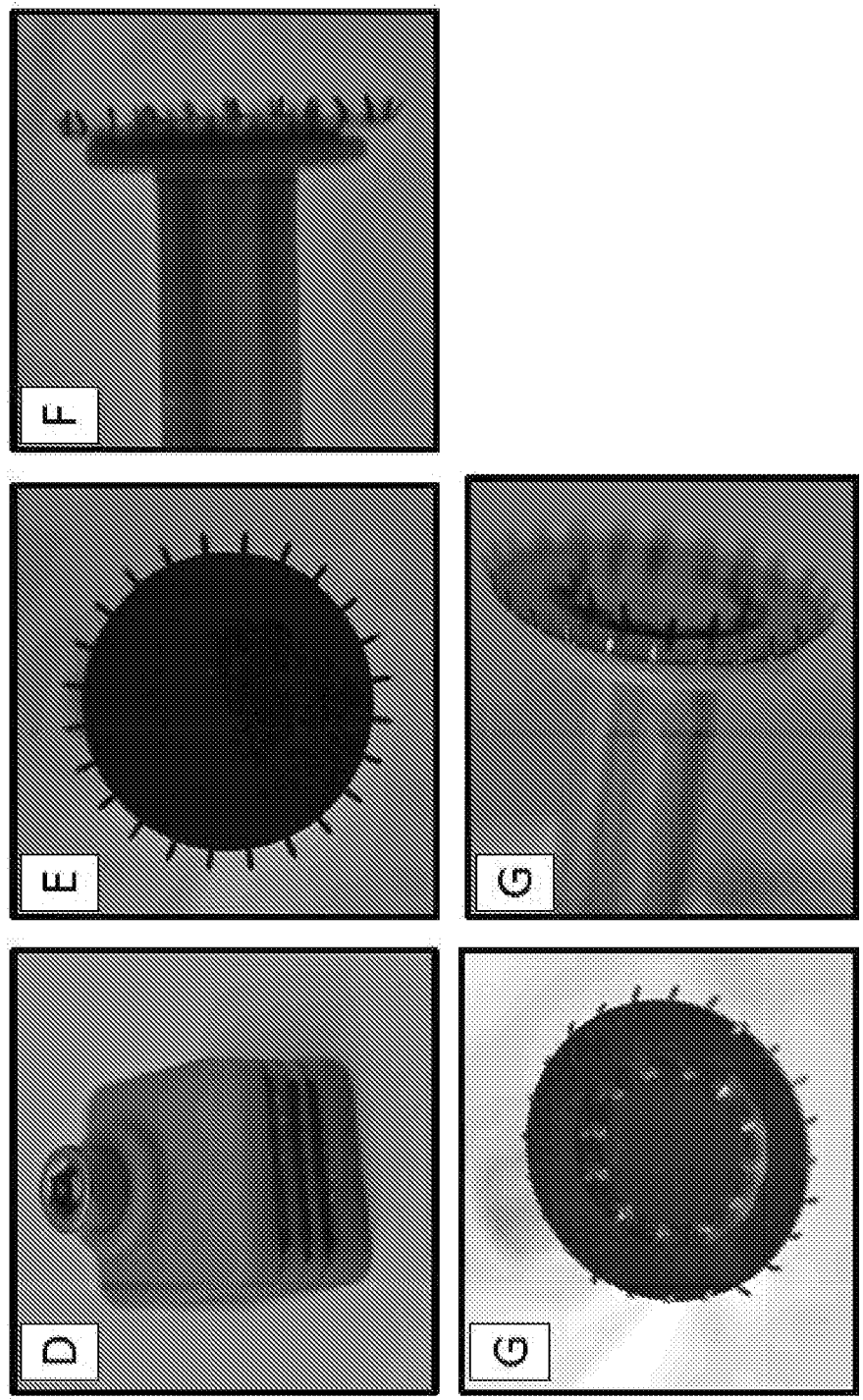
Figure 12:
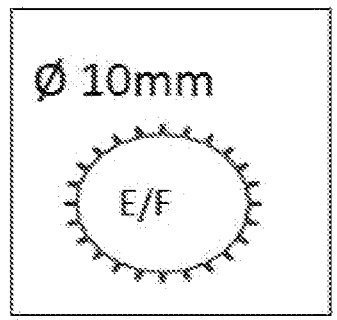
Figure 13:
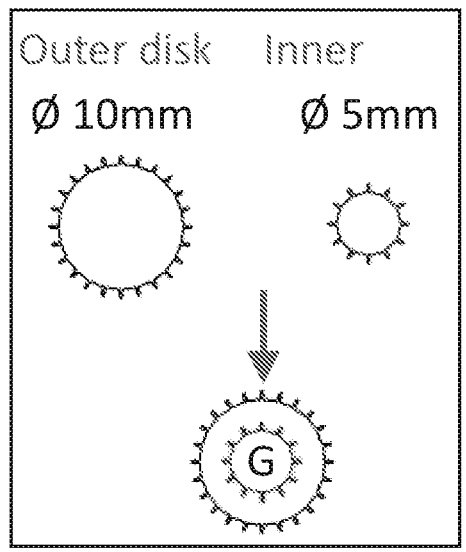
Figure 14:
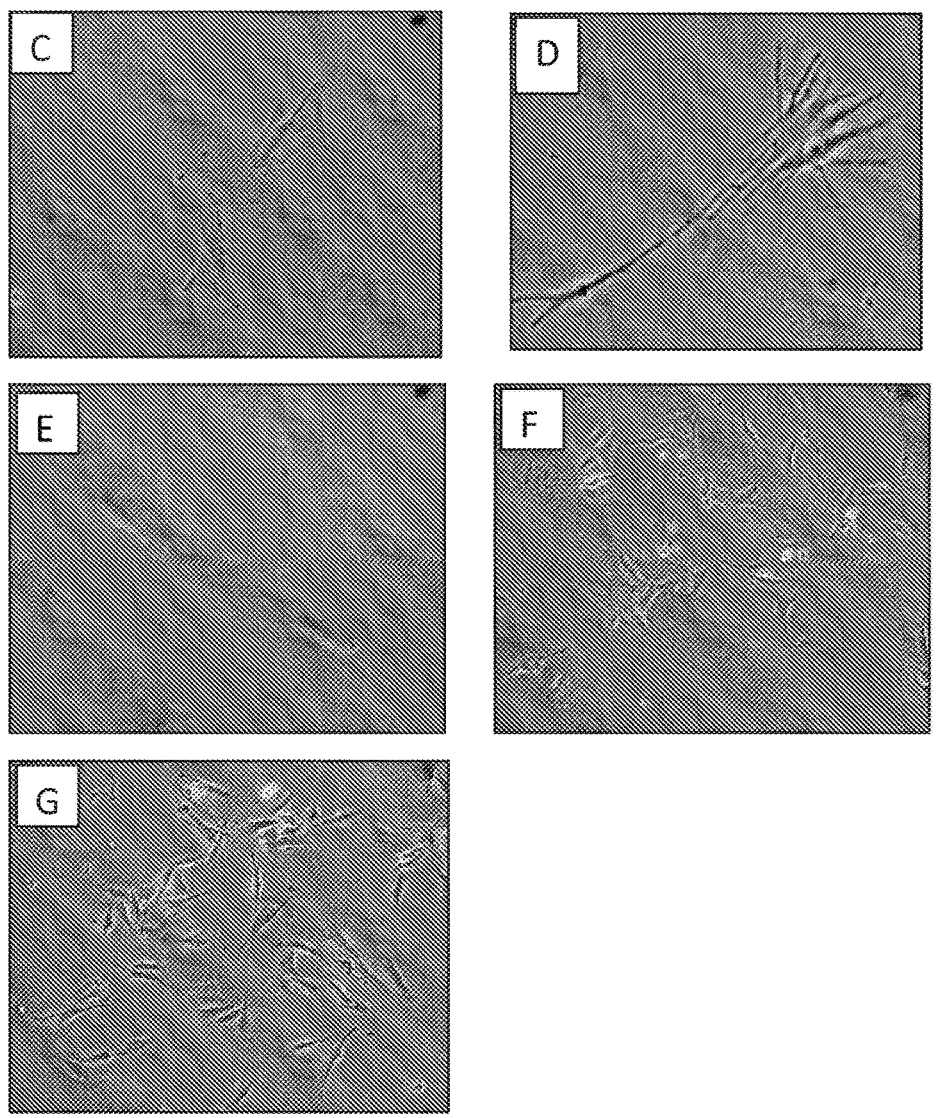
Figure 15:
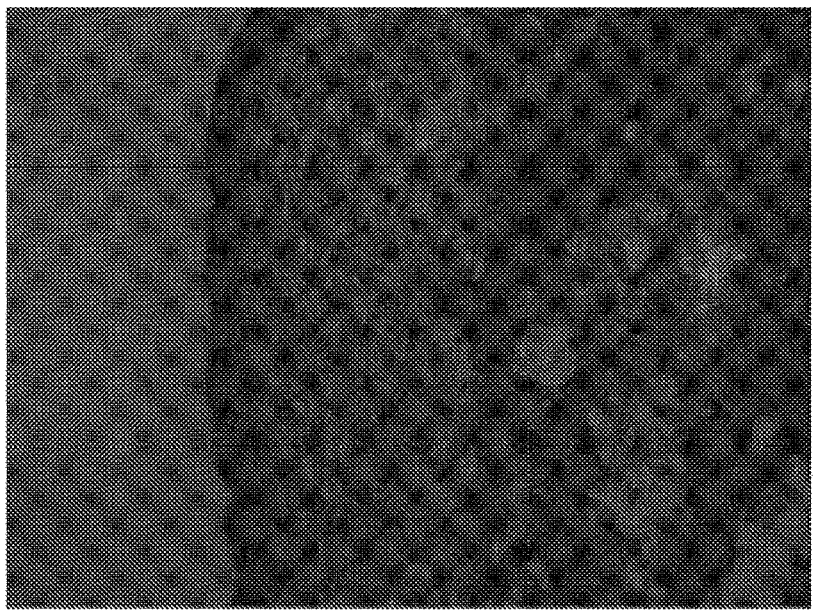
Figure 15:
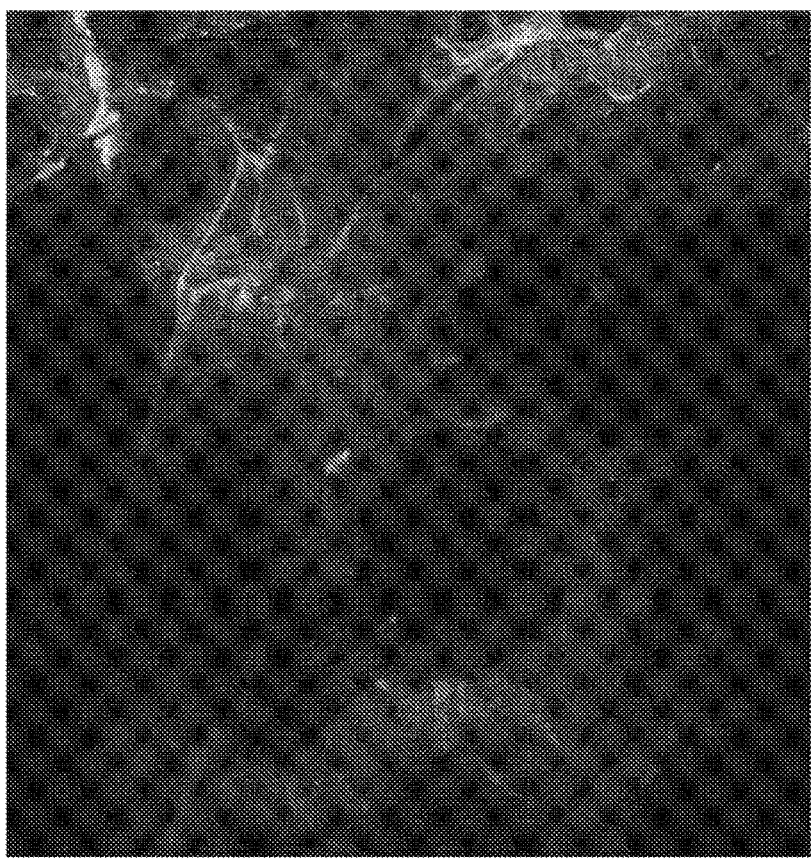

The Invention will now be described by way of example only with reference to the Examples below and to the following Figures wherein:

FIG. 1. Methylene blue staining to evaluate the diffusion of liquid through skin following microneedle injection;

FIG. 2. [A] Keratinocytes in culture, with the typical cobblestone appearance, [B] Melanocytes in culture, with the typical dendritic phenotype;

FIG. 3. Number of total keratinocytes counted after passing through microneedles with different bore sizes, divided into alive (blue) and dead (red) cells. The error bars represent the standard error on the means obtained on 3 repeats;

FIG. 4. Number of total melanocytes counted after passing through microneedles with different bore sizes, divided into alive (blue) and dead (red) cells. The error bars represent the standard error on the means obtained on 3 repeats;

FIG. 5. Keratinocytes in culture at 48 h after passing through microneedles with different bore sizes: 75 μm [A], 100 μm [B] and 150 μm [C];

FIG. 6. Melanocytes in culture at 48 h after passing through microneedles with different bore sizes: 75 μm [A], 100 μm [B] and 150 μm [C];

FIG. 7. Hooked microneedles for cell extraction before (top row) and after (bottom row) skin penetration, viewed using Scanning Electron Microscopy;

FIG. 8. Use of hollow microneedles for cell extraction, viewed using Scanning Electron Microscopy;

FIG. 9. Skin cells in culture at 96 h after collection from human skin by microneedle scraping;

FIG. 10. Human keratinocyte cells (stained blue with Hoechst staining) injected using microneedles at a concentration of 500,000 cells/50 μl into excised human breast skin. Skin was imaged using light and fluorescence microscopy. Skin autofluorescence appears as green. The white line denotes the skin surface;

FIG. 11. Shows pictures of the proprietary designs used to work the invention;

FIG. 12. Arrangement of microneedles on a supporting base member Design E and F; Disk diameter=10 mm; Number of needles per disk=24; Needles length=750 μm; Material: Stainless Steel; In design E the needles are in plane; In design F the needles are bent out of plane; Needles manufactured by wire Electrical Discharge Machining (EDM);

FIG. 13. A further arrangement of microneedles on a supporting base member, Design G: Outer disk diameter=10 mm; Number of needles in the outer disk=24; Inner disk diameter=5 mm; Number of needles in the inner disk=12; Total number of needles=36; Needles length=750 μm; Material: Stainless steel; The needles are all bent out of plane; Manufactured by wire EDM; The arrays are stacked and so the number of needles could be expanded easily;

FIG. 14. Shows images of the survival of extracted cells after passing through microneedles was also assessed. All the cells survived after passing through hollow microneedles with a bore size≥75 μm;

FIG. 15. Upper image shows that Hoechst labelled cells (blue nuclei) were injected in skin explants and successfully delivered to the dermis; lower image shows that the injected cells (blue nuclei) maintained their phenotype after injection in skin. Cells with a green cytoplasm are melanocytes, while cells with a red cytoplasm are keratinocytes; and Table 1 contains information relating to the efficiency of cell extraction using the specified microneedles, together with the technical features of each microneedle design.

Materials and Methods

Cell Source

Melanocytes and keratinocytes were isolated from non-affected skin (biopsy or cell scraping) or from the hair follicles. These were used directly or cultured to increase cell numbers.

Additionally, microneedle injection of primary melanocytes and keratinocytes obtained from commercial sources (Life Technologies) was also undertaken.

Cell Culture

Melanocytes and keratinocytes were expanded in vitro, using selective growth media.

For melanocytes, the selective growth media was Medium 254 (Life Technologies) or equivalent, supplemented with Human Melanocyte Growth Supplement-2, PMA-free (Life Technologies) or equivalent.

For keratinocytes, the selective growth media was Epi-Life Medium (Life Technologies) or equivalent, supplemented with Human Keratinocyte Growth Supplement (Life Technologies) or equivalent.

Cells were incubated at 37° C. in 5% $CO_2$ and media replaced every 48 to 72 h until a sufficient number of cells were obtained (determined depending on the extension of the area to be treated, approximately $10^5$ melanocytes/$cm^2$).

Extraction of viable live cells from the skin was assessed using light microscopy.

Cells were delivered to freshly excised human breast skin. A fraction of the cell culture was also stored in liquid nitrogen for subsequent application if needed, removing the need to repeat the isolation step.

Microneedle Delivery

Cells were delivered to the recipient site by the use of specifically designed microneedles. According to preliminary studies, using a marker dye instead of a cell suspension (FIG. 1), approximately 100 μL of a $10^6$ cells/mL solution was sufficient to re-pigment a skin area of approximately 1 $cm^2$, delivering $10^5$ cells to the area.

Microneedle Specifications

The microneedles used were hollow silicon microneedles, arranged in an array, to cover an area of approximately 0.5 $cm^2$.

Microneedles had a bore size between 75 and 150 μm, a wall thickness between 50 and 150 μm, spacing between 500 and 1000 μm, and a length between 300 and 700 μm.

Cell Extraction Using Microneedles

Different types of microneedles were used to perform cell extraction from skin. These included commercially available silicon microneedles (A, B, C) and our proprietary stainless steel microneedles (D, E, F, G).

Pictures of the proprietary stainless steel microneedle designs (D, E, F, G) are shown in FIG. 11. The specifications of these needles are as follow.

Design D: Array width=1.1 cm;
Number of needles per array=10;
Needles length=between 350 and 420 μm;
Number of arrays stacked=3;
Total number of microneedles=30;
Material: Stainless Steel. See FIG. 11D (made by Electrical Discharge Machining (EDM))
Design E and F: Disk diameter=10 mm;
Number of needles per disk=24;
Needles length=750 μm;
Material: Stainless Steel;
In design E the needles are in plane;
In design F the needles are bent out of plane;
Needles manufactured by wire Electrical Discharge Machining (EDM). See FIGS. 11E and F, and FIG. 12.
Design G: Outer disk diameter=10 mm;
Number of needles in the outer disk=24;
Inner disk diameter=5 mm;
Number of needles in the inner disk=12;
Total number of needles=36;
Needles length=750 μm;
Material: Stainless steel;
The needles are all bent out of plane;
Manufactured by wire EDM;
The arrays are stacked and so the number of needles could be expanded easily. See FIG. 11G and FIG. 13.

How the Microneedles are Used on Skin

Design A, B, C, and D: A 2 $cm^2$ area of the skin surface is scraped multiple time with a linear movement (left to right and right to left).

Design E: The disk is rolled multiple times on a 2 $cm^2$ area of the skin surface.

Design F and G: A 2 $cm^2$ area of the skin surface is scraped multiple times with a circular movement (clockwise).

After scraping, the material collected on the microneedles is transferred to a tube containing cold trypsin and incubated overnight at 4° C. The following day, the trypsin is inactivated with the same volume of serum. The cell containing solution is then filtered and centrifuged, and cells are resuspended, ready for injection.

With this method, different types of cells are extracted, including keratinocytes, melanocytes, fibroblasts, Merkel cells, Langerhans cells, macrophages, adipocytes, dendritic cells, etc.

The efficiency of cell extraction using these microneedles was assessed and it is reported in table 1 below, together with the technical features of each microneedle design.

After extraction, culturing the cells in a specific growth media (Medium 254 from Life Technologies or equivalent, supplemented with Human Melanocyte Growth Supplement-2, PMA-free from Life Technologies or equivalent) promotes melanocytes to differentiate from the pool of extracted cells, as shown in FIG. 14.

The survival of extracted cells after passing through microneedles was also assessed. All the cells survived after passing through hollow microneedles with a bore size≥75 μm.

Data Regarding Cell Injection

Cell survival has been tested after passing suspensions ranging from $10^5$ to $10^7$ cells/mL through different types of hollow microneedles. Cell survival is near 100% when cells at all these concentrations are injected thorough hollow microneedles with a bore size≥75 μm. Cell survival is significantly reduced if the cells are passed through hollow microneedles with smaller bore size, dropping to approximately 50% when the bore size is 50 μm.

Cell adhesion, cell proliferation, and cell phenotype are maintained after passing through microneedles with a bore size≥75 μm at all the concentrations tested.

Cell delivery to skin can be performed efficiently, with cells maintaining their original phenotype once injected, as shown in FIG. 15.

Results

Cell Delivery Through Microneedles

Cell cultures from commercially available human epidermal keratinocytes and melanocytes were established, and culturing conditions were optimized (FIG. 2).

Cell survival after passing through microneedles with different bore diameters (50, 60, 75, 100 and 150 μm) was tested using a $10^5$, $10^6$, $2\times10^6$ and $10^7$ cells/mL suspension. Trypan Blue staining was used to confirm cell viability. Both keratinocytes (FIG. 3) and melanocytes (FIG. 4) survived the procedure with all the concentrations tested when the bore diameter was greater than 60 μm. There was also no loss of cells during the procedure, showing that cells are not retained inside the microneedles.

The ability of cells to adhere to a surface and proliferate after passing through microneedles with different bore sizes (75, 100 and 150 μm) was tested. Both keratinocytes (FIG. 5) and melanocytes (FIG. 6) were able to attach to culture plates and proliferate after the procedure.

Cell Extraction from Skin Using Microneedles

We also used prototype microneedles to test the ability of microneedles to extract cells from the skin.

Firstly, we tested the ability of hooked stainless steel microneedles to extract skin cells after skin penetration (excised human breast skin) and removal (FIG. 7).

We also tested hollow microneedles using the same approach (FIG. 8).

Subsequently, as proof-of-concept, we also tested the ability of different types of solid and hollow microneedles to collect skin cells by scraping along the skin's surface (excised human breast skin). After scraping the skin, cells were detached from the microneedles by rinsing in culture media and captured in a culture plate.

Microneedle extraction of cells surprisingly allowed us to capture and culture a significant number of skin cells (FIG. 9).

In further studies we tested whether microneedles can deliver cells into relevant skin compartments. In these studies human keratinocytes were labelled prior to skin injection (excised human breast skin). Hollow microneedle delivery of 5000, 50000 and 500000 cells into excised human skin resulted in deposition of the cells in the upper dermis (FIG. 10).

Different types of microneedles were used to perform cell extraction from skin. These included commercially available silicon microneedles (A, B, C) and our own proprietary stainless steel microneedles (D, E, F, G).

Pictures of the stainless steel proprietary designs are shown in FIG. 11 with schematics showing the microneedles designs used in E, F and G shown in FIGS. 12 and 13.

After extraction, culturing the captured cells in a specific growth media promotes melanocytes to differentiate from the pool of extracted cells, as shown in FIG. 14 for designs C, D, E, F and G. The survival of extracted cells after passing through microneedles was also assessed. All the cells survived after passing through hollow microneedles with a bore size≥75 μm.

Cell adhesion, cell proliferation, and cell phenotype are maintained after passing through microneedles with a bore size≥75 μm at all the concentrations tested.

As further evidence of efficient cell delivery using microneedles, cells (with a blue nuclear cell staining) maintain their original phenotype once injected, as shown in FIG. 15.

SUMMARY

In summary our studies have shown that:

1) Cells can be collected from skin using microneedles;
2) Cells can be injected through hollow microneedles with a variety of bore diameters. All of the cells are injected with none retained, with high viability (cell survival is near 100%);
3) Cells can be injected into skin using microneedles.

This disclosed method therefore paves the way for a new minimally-invasive and pain-free approach wherein cells can be extracted and delivered to the various layers of the skin using microneedles, with little or no recovery time required.

| Type of microneedles used for extraction | Length of microneedles | Design name | Material | Number of cells extracted by scraping a 2 cm² area | Are melanocytes extracted and viable? |
|---|---|---|---|---|---|
| Hollow, 50 μm bore size | 450 μm | A | Silicon | $5 \times 10^5$ | NO |
| Hollow, 60 μm bore size | 600 μm | B | Silicon | $4 \times 10^5$ | NO |
| Hollow, 80 μm bore size | 750 μm | C | Silicon | $6 \times 10^5$ | YES 2 cells (0.0003%) |
| Solid, 3 rows of 10 microneedles | 350 to 420 μm | D | Steel | $5 \times 10^5$ | Yes 12 cells (0.0024%) |
| Solid, disk of 24 needles - in plane | 750 μm | E | Steel | $6 \times 10^5$ | YES 2 cells (0.0003%) |
| Solid, disk of 24 needles - out of plane | 750 μm | F | Steel | $8 \times 10^5$ | YES approximately 120 cells (0.015%) |
| Solid, 2 concentric disks, total of 36 needles - out of plane | 750 μm | G | Steel | $1 \times 10^6$ | YES approximately 300 cells (0.03%) |

The invention claimed is:

1. A device for skin improvement or repair comprising: a plurality of microneedles attached to or integral with a supporting base member and arranged in at least one circular pattern on same wherein said microneedles are hollow and have a bore size of between 75-150 μm diameter and a length of between 250 μm and 1000 μm, wherein the device is adapted for (a) extracting cells from a first area of skin of an individual, and subsequently (b) injecting said cells into a second area of skin of said individual, wherein there is no observed loss of viability of said cells as a result of the transplantation process; and whereby said second area of skin is improved by the transplantation of said cells.

2. The device according to claim 1 wherein in step (b), said cells are injected into the viable epidermis, papillary.

3. The device according to claim 1 wherein said microneedles have a bore size of 75-150 μm diameter.

4. The device according to claim 1 wherein a plurality of concentric circular patterns of microneedles is provided on said base member.

5. The device according to claim 4 wherein two concentric circular patterns of microneedles are provided on said base member.

6. The device according to claim 1 wherein said microneedles are attached to or integral with said base member so that their longitudinal axis is normal to the supporting axis of said base member or so that their longitudinal axis is at an angle to the supporting axis of said base member such that said microneedles splay outwards with respect to the supporting axis of said base member.

7. The device according claim 1 wherein between 6 and 48 microneedles are used in each of said circular patterns.

8. The device according to claim 1 wherein 24 microneedles are used in an outer concentric circular pattern and 12 microneedles are used in an inner concentric circular pattern.

9. The device according to claim 1 wherein said microneedles are between 250 μm and 1000 μm in length.

10. The device according to claim 1 wherein said microneedles are about 750 μm in length.

11. The device according to claim 1 wherein said microneedles are made from a polymer, co-polymer, polysaccharide, sugar, silicon or steel.

12. A method for skin improvement or repair comprising:
   a) extracting with a plurality of microneedles attached to a supporting base member and arranged in at least one circular pattern on same at least one cell from a first area of skin of an individual to be treated; and
   b) injecting with at least one hollow microneedle, having a bore size of 75-150 μm and a length of between 250 μm and 1000 μm, said cell(s) into a second area of skin; whereby said second area of skin is improved by the transplantation of said cell(s) therein wherein there is no observed loss of viability of said cells as a result of the transplantation process; and whereby said second area of skin is improved by the transplantation of said cells.

13. The method according to claim 12 wherein said bore size is between 75 and 150 μm diameter.

14. The method according to claim 12 wherein said injecting also involves the use of a single microneedle or a plurality of microneedles attached to a supporting base member and where a plurality of microneedles are used they are arranged in at least one row, rectangular array or circular pattern on same.

15. The method according to claim 12 wherein said cell(s) are selected from the group comprising: melanocytes, keratinocytes, dermal fibroblasts, corneocytes, Langerhans cells, dermal dendritic cells, epidermal stem cells, Merkel cells, mast cells, macrophages, T-cells, dermal sheath cells or follicular outer root sheath cells.

16. The method according to claim 12 wherein in step b) said cell(s) are injected into the viable epidermis, papillary dermis or reticular dermis layers of the skin.

17. The method according to claim 12 wherein the microneedles used in step a) are different to that/those used in step b).

18. The method according to claim 12 wherein said method is repeated for all areas of the skin for which repair or improvement is desired.

19. The method according to claim 12 wherein said cell(s) extracted in step a) are preserved prior to the performance of step b).

20. The method according to claim 19 wherein said cell(s) extracted in step a) are preserved prior to the performance of step b) and further, wherein said preserved cell(s) are used for repeated procedures whereby measured amounts of the preserved cells are repeatedly used for the repeated performance of step b).

21. The method of claim 12 wherein no loss of cell viability occurs.

* * * * *